(12) United States Patent
Kronstedt et al.

(10) Patent No.: US 10,285,607 B2
(45) Date of Patent: May 14, 2019

(54) WEARABLE PATCH WITH RIGID INSERT

(71) Applicant: Preventice Technologies, Inc., Rochester, MN (US)

(72) Inventors: Brian Kronstedt, Shoreview, MN (US); Andrew Arroyo, Austin, TX (US); Charles Rector, Edina, MN (US)

(73) Assignee: Preventice Technologies, Inc., Rochester, MN (US)

( * ) Notice: Subject to any disclaimer, the term of this patent is extended or adjusted under 35 U.S.C. 154(b) by 297 days.

(21) Appl. No.: 15/214,904

(22) Filed: Jul. 20, 2016

(65) Prior Publication Data

US 2018/0020942 A1    Jan. 25, 2018

(51) Int. Cl.
*A61B 5/0408* (2006.01)
*A61B 5/00* (2006.01)

(52) U.S. Cl.
CPC ...... *A61B 5/04085* (2013.01); *A61B 5/04087* (2013.01); *A61B 5/6833* (2013.01)

(58) Field of Classification Search
CPC ... A61B 5/04085; A61B 5/0476; A61B 5/048; A61B 5/0492; A61B 5/0416
USPC ................................ 600/391–394
See application file for complete search history.

(56) References Cited

U.S. PATENT DOCUMENTS

| | | | | |
|---|---|---|---|---|
| 3,845,757 A | * | 11/1974 | Weyer | A61B 5/0408 600/391 |
| 3,989,035 A | * | 11/1976 | Zuehlsdorff | A61B 5/0408 600/391 |
| 5,402,780 A | * | 4/1995 | Faasse, Jr. | A61B 5/0408 29/877 |
| 5,406,945 A | * | 4/1995 | Riazzi | A61B 5/0408 600/394 |
| 5,511,548 A | * | 4/1996 | Riazzi | A61B 5/0408 600/391 |
| 8,449,469 B2 | * | 5/2013 | Banet | A61B 5/021 600/438 |

FOREIGN PATENT DOCUMENTS

WO    2014/10018    * 12/2013

\* cited by examiner

*Primary Examiner* — Lee S Cohen
(74) *Attorney, Agent, or Firm* — Patterson + Sheridan, LLP

(57) ABSTRACT

Embodiments of the present disclosure generally relate wearable patches having rigid inserts. The rigid insert is positioned adjacent to one or more connectors, such as studs for receiving sockets to distribute the force transferred to a patient when reconnecting a socket to the stud. The rigid insert may be sized to maintain flexibility in areas of the wearable patch. An optional adhesive layer may be applied to the wearable patch adjacent the rigid insert to reduce the likelihood of delamination of the wearable patch.

19 Claims, 3 Drawing Sheets

WEARABLE PATCH WITH RIGID INSERT

BACKGROUND

Field

Embodiments of the present disclosure generally relate to wearable patches.

Description of the Related Art

Wearable patch products, such as ECG electrodes or the BodyGuardian® Strip available from Preventice Solutions® of Rochester, Minn., are used to couple a sensor or other device to a patient's body. The wearable patches include connectors, such as studs for receiving sockets, so that sensors may be selectively removed and optionally reapplied to the patch, as desired. However, reapplication of the sensor on-body requires forcibly pushing a socket connector onto a stud. The pressure applied during reconnection may be uncomfortable for a patient, and may even cause bruising. To avoid this discomfort, some patients may choose to discard the wearable patch, and instead apply a new patch directly to the sensor off-body. The new patch having the sensor already coupled thereto may then be adhered to the patient's body, avoiding an uncomfortable connection. However, since wearable patches do not need to be discarded with every disconnection/reconnection of a sensor, this method results in increased costs for a patient or healthcare provider due to excessive turnover of wearable patches.

SUMMARY

Embodiments of the present disclosure generally relate wearable patches having rigid inserts. The rigid insert is positioned adjacent to one or more connectors, such as studs for receiving sockets, to distribute the force transferred to a patient when reconnecting a socket to the stud. The rigid insert may be sized to maintain flexibility in areas of the wearable patch. An optional adhesive layer may be applied to the wearable patch adjacent the rigid insert to reduce the likelihood of delamination of the wearable patch.

In one aspect, a wearable patch comprises a base layer; a coversheet disposed above the base layer; an electrically conductive layer positioned between the base layer and the coversheet; a rigid insert positioned between the base layer and the coversheet; and one or more studs for socket connections aligned with the rigid insert.

In another aspect, a wearable patch comprises a base layer; an intermediate layer comprising an adhesive positioned over the base layer; a rigid insert positioned over the intermediate layer; an adhesive layer positioned over the rigid insert; an electrically conductive layer positioned over the adhesive layer; a coversheet positioned over the electrically conductive layer; and one or more studs for socket connections aligned with the rigid insert.

In another aspect, a wearable patch comprises a base layer; an intermediate layer comprising an adhesive positioned over the base layer; a rigid insert positioned over the intermediate layer, wherein the rigid insert has a thickness within a range of about 0.3 millimeters to about 1.5 millimeters; an adhesive layer positioned over the rigid insert; an electrically conductive layer positioned over the adhesive layer; a coversheet positioned over the electrically conductive layer; and one or more studs for socket connections aligned with the rigid insert.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the appended drawings. It is to be noted, however, that the appended drawings illustrate only exemplary embodiments and are therefore not to be considered limiting of its scope, and the disclosure may admit to other equally effective embodiments.

Figure 1:
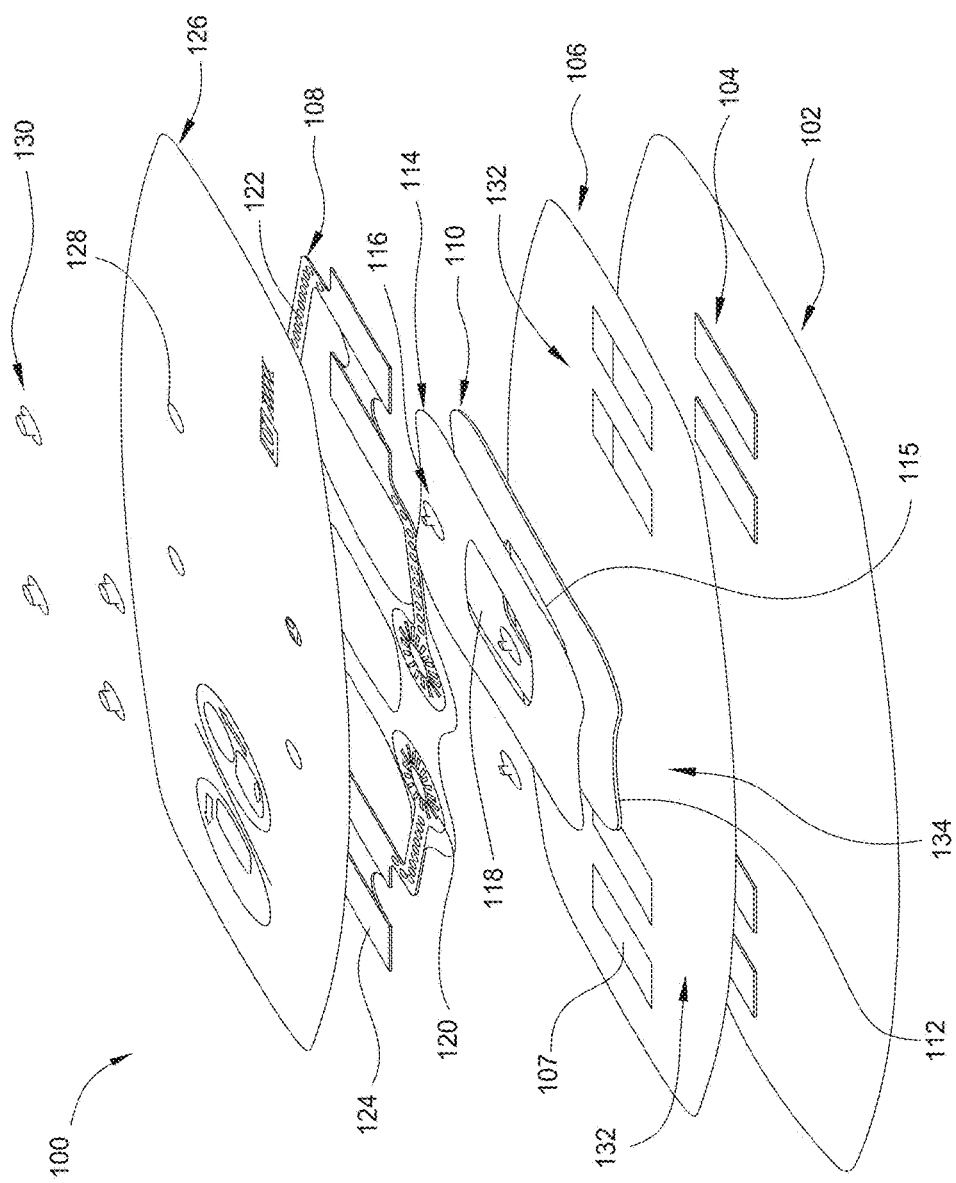
FIG. 1 illustrates a schematic exploded view of a wearable patch having a rigid insert, according to one aspect of the disclosure.

To facilitate understanding, identical reference numerals have been used, where possible, to designate identical elements that are common to the figures. It is contemplated that elements and features of one aspect or embodiment may be beneficially incorporated in other aspects or embodiments without further recitation.

DETAILED DESCRIPTION

Embodiments of the present disclosure generally relate wearable patches having rigid inserts. The rigid insert is positioned adjacent to one or more connectors, such as studs for receiving snaps, to distribute the force transferred to a patient when reconnecting a socket to the stud. The rigid insert may be sized to maintain flexibility in areas of the wearable patch. An optional adhesive layer may be applied to the wearable patch adjacent the rigid insert to reduce the likelihood of delamination of the wearable patch.

FIG. 1 illustrates a schematic exploded view of a wearable patch 100 having a rigid insert, according to one aspect of the disclosure. The wearable patch 100 includes a base layer 102. The base layer 102 may serve as a liner to protect a conductive material 104 and an intermediate layer 106 during shipping and handling, but is removed prior to application to a patient's body. In one example, the base layer 102 may cover and extend beyond adhesive layer 106 for easy removal from the intermediate layer 106. The base layer 102 may be a vacuum-formed polyethylene terephthalate liner, which may have a thickness within a range of about 100 microns to about 250 microns, such as about 160 microns. An electrically conductive material 104, such as a hydrogel, is positioned in contact with the electrically conductive pads 124 (four are shown). The conductive material 104 may be positioned within the intermediate layer 106 in spaced apart areas (four are shown). As illustrated in FIG. 1, the conductive material 104 may cover rectangular areas, but other shapes and configurations are also contemplated. Suitable conductive materials include and Axelgaard® AG635.

The intermediate layer 106 is positioned above the base layer 102. The intermediate layer may be an adhesive layer, such as a double-sided tape. In one example, the intermediate layer 106 is a non-woven tape, such as 3M 9917. The intermediate layer 106 may be a polyester/rayon blend having an acrylate adhesive applied to each side thereof. The intermediate layer 106 may be breathable to facilitate patient comfort. One or more openings 107 are formed through the intermediate layer 106. The openings 107 are aligned with the adhesive 104 to allow contact between the conductive material 104 and an electrically conductive layer 108 positioned above the intermediate layer 106.

A rigid insert 110 is positioned above and adhered to the intermediate layer 106. The rigid insert 110 has lateral (x-direction) and transverse (y-direction) dimensions less than the intermediate layer 106 and the base layer 102. The relatively smaller dimensions of the rigid insert 110 allow the wearable patch 100 to maintain some flexibility, thus improving patient fit and comfort. The rigid insert also includes concave edges 112. The concavity of the edges 112 spaces the rigid insert further form the perimeter of the wearable patch 100, thus increasing adhesion of the layers of the wearable patch 100. In one example, the edges of the rigid insert 110 may be spaced about 5 millimeters from the outward edges of the wearable patch 100. It is contemplated that the spacing may be adjusted depending on the adhesive properties of components of the wearable patch 100.

The increased adhesion between layers of the wearable patch 100 reduces the likelihood of delamination of the wearable patch. The rigid insert 110 may also include an opening 115 formed centrally therein to increase breathability of the wearable patch 100. However, more openings, or other locations for the opening(s), are also contemplated. The rigid insert 110 may be formed form plastic, such as acrolynitrile butadiene styrene (ABS), and may have a thickness within a range of about 0.3 millimeters to about 1.5 millimeters, such as about, 0.5 millimeters to about 1 millimeter. The thickness or material of the rigid insert 110 may be selected to provide the desired rigidity to the wearable patch 100.

An adhesive layer 114 is positioned on and in contact with the rigid insert 110. The adhesive layer 114 may be a pressure sensitive adhesive having a similar shape or the same shape as the rigid insert 110. The adhesive layer 114 also includes an opening 118 therein to facilitate breathing of the wearable patch 100. The opening 118 may be sized similar to and aligned with the opening 115 that is formed through the rigid insert 110. The adhesive layer 114 may be adhesive on both the upper and lower surfaces thereof. The adhesive layer 114 facilitates securing of one or more eyelets 116 (four are shown) within the wearable patch 100, as well as facilitates reduced delamination of the wearable patch 100.

The one or more eyelets 116 are adhered to an upper surface of the adhesive layer 114. The one or more eyelets 116 are aligned with and received in openings 120 formed in an electrically conductive layer 108. The electrically conductive layer 108 is positioned above the adhesive layer 114, and includes a conductive pathway 122. The conductive pathway 122 may include silver or other metals, and may facilitate electrical conductivity within the wearable patch 100. In one example, the conductive pathway 122 may be a metal, or may be a polymeric material having conductive particles embedded therein. Other electrically conductive pathways are also contemplated. Additionally, the electrically conductive layer 108 includes one or more electrically conductive pads 124 (four are shown) aligned with the openings 107 and the conductive material 104 to create an electrical connection with the conductive material 104. The electrical conductivity within the wearable patch 100 facilitates collection of biometric data from a patient.

A coversheet 126 is positioned over the electrically conductive layer 108. The coversheet 126 is an outer protective layer of the wearable patch 100. The coversheet 126 may display print, such as a logo or instructions, thereon. The coversheet 126 may be a polyurethane and/or polyolefin nonwoven film, and may include an optional adhesive, such as an acrylate adhesive, on lower surface thereof. In one example, the coversheet 126 is both elastic and breathable. An exemplary coversheet 126 is 3M™ Nonwoven Elastic Medical Tape 9907W. The coversheet includes a plurality of openings 128 (four are shown) formed therein. The openings 128 correspond to and align with each of the eyelets 116 to allow passage of the eyelets 116 through the coversheet 126. Studs 130 are secured to the eyelets 116 on an upper surface of the coversheet 126. The studs 130 facilitate connection of a sensor device to the wearable patch 100 via snap connection.

The inclusion of the rigid insert 110 increases patient comfort during connection of a sensor or other device. As illustrated in FIG. 1, the eyelets 116 and the studs 130 are aligned with the rigid insert 110. As pressure is applied to "snap" a sensor, lead cable, or other device onto the studs 130, the applied force is transferred to and distributed amongst the surface area of the rigid insert 110. The distributed force results in a reduced pressure applied to the patient, thus resulting in a more comfortable application process and a reduced likelihood of bruising. Additionally, the rigidity of the rigid insert not only increases patient comfort during the application process, but also eases the application process by providing a solid base during sensor application. It is contemplated that any rigid insert 110 which increases the area of applied force may provide improved patient comfort.

As noted above, the rigid insert 110 extends laterally on transversely only part way across the wearable patch 100. Thus, lateral areas 132 (two are shown) and transverse areas 134 (one of two is shown) remain flexible to increase patient comfort while the wearable patch is adhered to the patient. It is contemplated that the relative size between the rigid insert 110 and the areas 132, 134 may be adjusted to provide the desired relationship between rigidity and flexibility.

Figure 2:
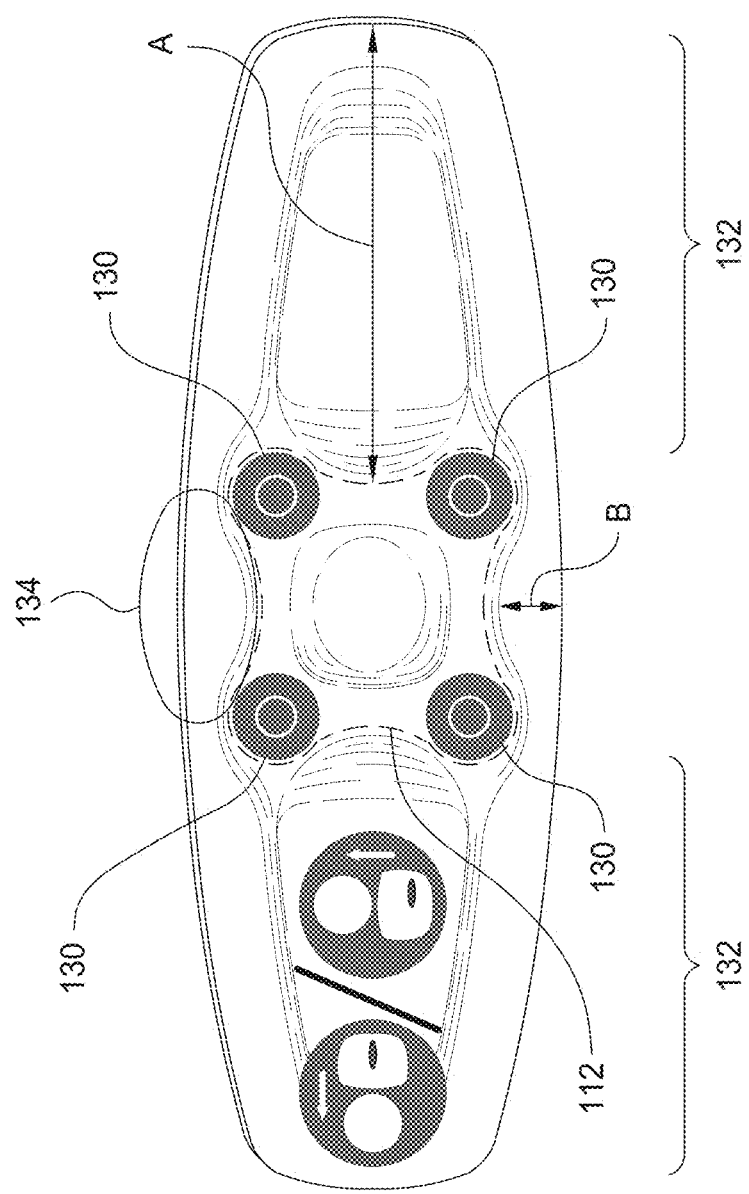
FIG. 2 illustrates a top view of the wearable patch of FIG. 1.

FIG. 2 illustrates a top view of the wearable patch 100 of FIG. 1. The wearable patch 100 includes four studs 130 exposed through the coversheet 126. A rigid insert 110, shown in phantom, is positioned beneath the studs 130 to provide a solid base when securing a sensor or other device to the studs 130 via a snap connection. The concave edges 112 of the rigid insert 110 are spaced a distance A from the lateral edges of the wearable patch 100, defining areas 132, while other concave edges 112 are spaced a distance B from the transverse edges of the wearable patch 100, thus defining areas 134. The size of the rigid insert 110 and the degree of concavity of the edges 112 may be selected to provide desired distances A and B to reduce or eliminate delamination of the wearable patch 100, or to provide the desired amount of flexibility to the wearable patch 100. While the rigid insert 110 has a generally rectangular shape, other shapes are also contemplated.

Figure 3:
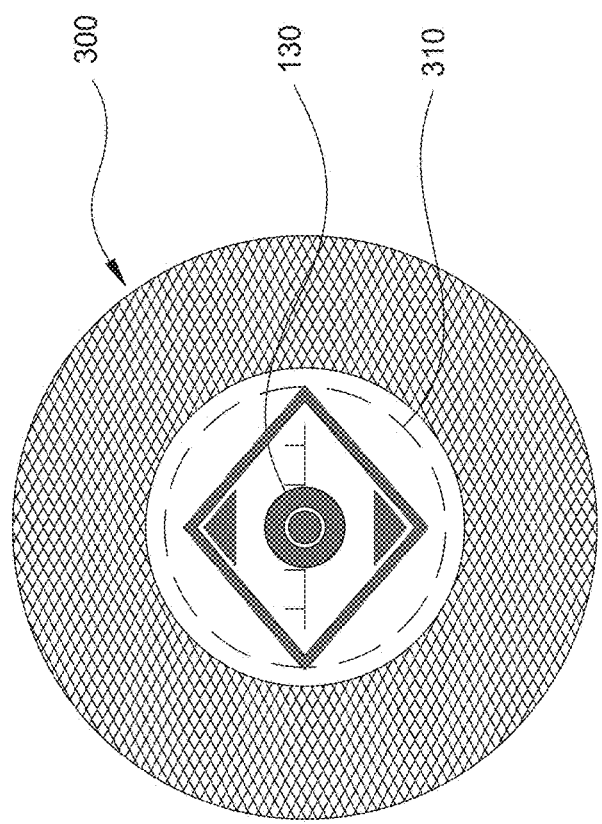
FIG. 3 illustrates a wearable patch having a rigid insert, according to another aspect of the disclosure.

FIG. 3 illustrates a wearable patch 300 having a rigid insert, according to another aspect of the disclosure. The wearable patch 300 may be an EKG or ECG electrode, for example. The wearable patch 300 is similar to the wearable patch 100, and may include any or all of the components of the wearable patch 100. For example, the wearable patch 300 may include a base layer, a rigid insert, an electrically conductive layer, an eyelet, a stud, and a coversheet. The wearable patch 300 may also include one or more adhesives to affix the components to one another, or to adhere the wearable patch to a patient.

In contrast to the wearable patch 100, the wearable patch 300 is circular in shape, and includes only a single stud 130. In such an example, a rigid insert 310 (shown in phantom) may be selected to have a similar shape to the wearable patch 300. For example, the rigid insert 310 of the wearable patch 300 may have a circular shape with a diameter less than the diameter of the wearable patch 300. The rigid insert 310 may be centrally positioned with respect to the stud 130. In such an example, the rigid insert 310 may lack an opening formed therein, such as opening 118 shown in FIG. 1. As similarly described above with respect to the wearable patch 100, the presence of the rigid insert 310 in the wearable patch 300 results in an easier and more comfortable snap connection to the stud 130.

Benefits of aspects of the disclosure include increased patient comfort when connecting sensors or leads to a wearable patch due to the distribution of applied force. Benefits also include ease of connection due to the rigidity of the wearable patch adjacent a stud of a snap connection. The resultant increase in patient comfort may foster a longer duration of electrode wear, reduced number of electrodes used over a given time period, and consequently a lower electrode cost. Moreover, wearable patches disclosed herein maintain breathability and flexibility to further increase patient comfort during normal wear.

While the foregoing is directed to embodiments of the present disclosure, other and further embodiments of the disclosure may be devised without departing from the basic scope thereof, and the scope thereof is determined by the claims that follow.

What is claimed is:

1. A wearable patch, comprising:
   a base layer;
   a coversheet disposed above the base layer;
   an electrically conductive layer positioned between the base layer and the coversheet, the electrically conductive layer comprising one or more electrically conductive pads;
   a rigid insert positioned between the base layer and the coversheet; and
   a plurality of connectors for snap connections, wherein the connectors are electrically coupled to the electrically conductive layer, and wherein the rigid insert is sized to align with the plurality of connectors, is not aligned with the electrically conductive pads, and is smaller in size than the base layer and the coversheet.

2. The wearable patch of claim 1, wherein the rigid insert comprises plastic.

3. The wearable patch of claim 1, wherein the rigid insert comprises acrolynitrile butadiene styrene.

4. The wearable patch of claim 1, wherein the rigid insert has a thickness within a range of about 0.5 millimeters to about 1 millimeter.

5. The wearable patch of claim 1, wherein the rigid insert includes an opening formed therein.

6. The wearable patch of claim 1, further comprising an adhesive layer located between the rigid insert and the electrically conductive layer.

7. The wearable patch of claim 6, wherein the adhesive layer has the same shape as the rigid insert.

8. The wearable patch of claim 1, wherein the connectors for snap connections comprise studs.

9. The wearable patch of claim 1, wherein the rigid insert comprises a plurality of concave outer edges.

10. A wearable patch, comprising:
    a base layer;
    an intermediate layer comprising an adhesive positioned over the base layer;
    a rigid insert positioned over the intermediate layer;
    an adhesive layer positioned over the rigid insert;
    an electrically conductive layer positioned over the adhesive layer, the electrically conductive layer comprising one or more electrically conductive pads;
    a coversheet positioned over the electrically conductive layer; and
    a plurality of connectors for snap connections, wherein the connectors are electrically coupled to the electrically conductive layer, and wherein the rigid insert is sized to align with the plurality of connectors, is not aligned with the electrically conductive pads, and is smaller in size than the base layer and the coversheet.

11. The wearable patch of claim 10, wherein the rigid insert includes an opening formed therein.

12. The wearable patch of claim 10, wherein the rigid insert comprises plastic.

13. The wearable patch of claim 10, wherein the rigid insert comprises acrolynitrile butadiene styrene.

14. The wearable patch of claim 10, wherein the rigid insert has a thickness within a range of about 0.5 millimeters to about 1 millimeter.

15. The wearable patch of claim 10, wherein the adhesive layer has the same shape as the rigid insert.

16. The wearable patch of claim 15, wherein the rigid insert includes concave outer edges.

17. The wearable patch of claim 10, further comprising eyelets in contact with the connectors, wherein the eyelets are aligned with the rigid insert.

18. The wearable patch of claim 10, wherein the connectors for snap connections comprise studs.

19. A wearable patch, comprising:
    a base layer;
    an intermediate layer comprising an adhesive positioned over the base layer;
    a rigid insert positioned over the intermediate layer, wherein the rigid insert has a thickness within a range of about 0.3 millimeters to about 1.5 millimeters;
    an adhesive layer positioned over the rigid insert;
    an electrically conductive layer positioned over the adhesive layer, the electrically conductive layer comprising one or more electrically conductive pads;
    a coversheet positioned over the electrically conductive layer; and
    a plurality of connectors for snap connections, wherein the connectors are electrically coupled to the electrically conductive layer, and wherein the rigid insert is sized to align with the plurality of connectors, is not aligned with the electrically conductive pads, and is smaller in size than the base layer and the coversheet.

* * * * *